Figure 2:
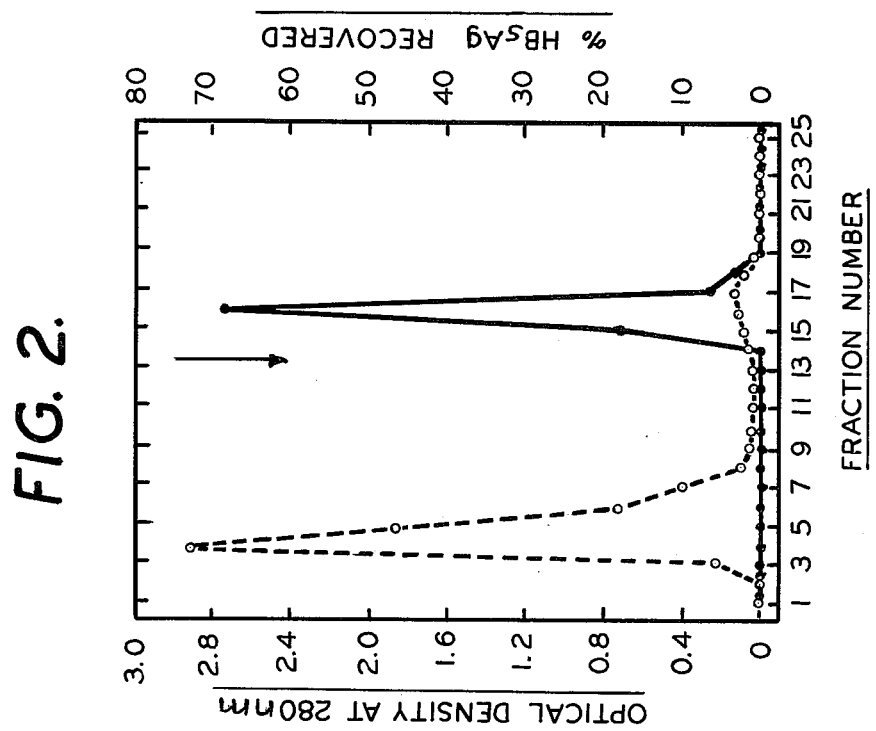

United States Patent [19]

Neurath

[11] 3,976,767

[45] Aug. 24, 1976

[54] PURIFICATION OF HEPATITIS B SURFACE ANTIGEN BY CHROMATOGRAPHY ON AGAROSE CONTAINING AMINOALKYL RESIDUES

[75] Inventor: A. Robert Neurath, New York, N.Y.

[73] Assignee: The New York Blood Center, New York, N.Y.

[22] Filed: Apr. 14, 1975

[21] Appl. No.: 568,093

[52] U.S. Cl. .................................... 424/89; 195/1.5
[51] Int. Cl.² ...................... A61K 39/12; C12K 5/00
[58] Field of Search ......................... 195/1.5; 424/89

[56] References Cited
OTHER PUBLICATIONS

Kenyon et al. – Science vol. 179, (Jan. 12, 1973), pp. 187–189.

*Primary Examiner*—Sam Rosen
*Attorney, Agent, or Firm*—Burgess, Dinklage & Sprung

[57] ABSTRACT

A process for separating hepatitis B surface antigen from a mixture containing the same which comprises passing said mixture over an agarose gel containing terminal aminononyl or aminodecyl groups to thereby deposit on said gel said hepatitis B surface antigen while allowing other components of said mixture to pass therethrough and thereafter eluting said hepatitis B surface antigen by passing an eluting agent over said agarose gel containing hepatitis B surface antigen.

7 Claims, 2 Drawing Figures

PURIFICATION OF HEPATITIS B SURFACE ANTIGEN BY CHROMATOGRAPHY ON AGAROSE CONTAINING AMINOALKYL RESIDUES

BACKGROUND OF THE INVENTION

1. Field of the Invention

This invention relates to the purification of hepatitis B surface antigen. More especially this invention relates to a purification of such hepatitis B surface antigen by removal therefrom of other components which are in admixture therewith. This invention is particularly concerned with the selective removal of hepatitis B surface antigen from other proteinaceous material in a blood fraction or in human serum.

2. Discussion of the Prior Art

Numerous attempts have been made to purify hepatitis B surface antigen. These attempts have been made since a prerequisite for a vaccine is a purified hepatitis B surface antigen. The purification of hepatitis B surface antigen has taken a number of routes. One of such routes involves the use of immunosorbents. These immunosorbents represent the most selective tool for the isolation and purification of antigens. However, their use in large purification is not a practical route inasmuch as the supply of mono-specific antibodies may be limited.

As a result thereof, chromatographic techniques based on less specific interactions that those involved in immunologic recognition has proved to be advantageous for the separation of virus antigens from contaminating proteins. One approach to the purification of hepatitis B surface antigen has been to utilize a lectin, concanavalin A which has been insolubilized on agarose gel. Thus, there is described in Neurath, A. R.; Prince, A. M.; and Lippin, A. (1973) Affinity chromatography of hepatitis B antigen on concanavalin A linked to Sepharose, *Journal of General Virology* 19, 391–395. The Separation of Hepatitis B surface antigen from human serum has been achieved by isopycnic and rate zonal centrifugations-techniques requiring expensive equipment. Gerin, J. L.; Holland, P. V.; and Purcell, R. H. (1971): Australia antigen: Large scale purification from human serum and biochemical studies of its proteins; *Journal of Virology* I, 569–576.

In search for alternative techniques which are more amenable to a scaling up of the separation technique, attention has been directed to hydrophobic chromatography. Hydrophobic chromatography has been employed in the separation of proteins differing in frequency and size of exposed hydrophobic regions (Shaltiel & Er-El (1973). Hydrophobic chromatography: Use for Purification of Glycogen Synthetase. *Proceedings of the National Academy of Sciences of the United States of America* 70, 778–781. It became desirable to provide a process which is useful in large scale purification of hepatitis B antigen and to provide a process which would substantially further purify and concentrate hepatitis B surface antigen which had previously undergone a separation technique such as by the use of insolubilized concanavalin A or by treatment with polyethylene glycol.

SUMMARY OF THE INVENTION

In accordance with the present invention hepatitis B surface antigen is purified and concentrated by a process which comprises passing a mixture thereof over an agarose gel containing terminal aminononyl or aminodecyl groups to thereby deposit onto said gel said hepatitis B surface antigen while allowing other components of the mixture to pass therethrough and thereafter eluting said hepatitis B surface antigen by passing an eluting agent over said agarose gel.

In accordance with this invention, it has been discovered that certain alpha, omega-diaminoalkanes linked to an agarose gel are useful for the selective adsorption of hepatitis B surface antigen from a mixture containing the same. Specifically, it has been found that hepatitis B antigen can be purified from serum if the serum is passed over an agarose gel which has aminononyl or aminodecyl groups.

As a first step in the process of the invention, there is obtained an agarose gel. The agarose gel can be a material sold commercially under the name Sepharose 2B or Sepharose 4B, which material is available commercially from Pharmacia in Uppsala, Sweden. Other forms of agarose gel can also be obtained. The material is thereafter activated by treatment with a CN-halide suitably CNBr or CNI. It has been found that such treatment activates the agarose gel although the precise chemical phenomenon is not known. The CN-halide treatment places onto the agarose gel a group which reacts with amino groups. Thereafter, the CN-halide activated agarose gel is further treated with a large excess of an alpha, omega-diaminoalkane, having 9 or 10 carbon atoms in the chain. It has been found, surprisingly, that other alpha, omega-diaminoalkanes are not useful in the treatment of the CN-halide activated agarose gel because they leave a chemical substituent thereon which is not sufficiently specific for the hepatitis B surface antigen.

In any event, the CN-halide activated agarose gel is treated with between about $10^{-3}$ to $10^{-2}$ moles of $C_9$-$C_{10}$ alpha, omega-diaminoalkane per ml. of agarose gel. Generally speaking, the diamine in water-dimethylformamide is mixed with the agarose gel until the agarose gel reacted with the maximum amount of diaminoalkane. Generally speaking, there are between 1 and 30 $\mu$ moles aminoalkyl groups per ml. of adsorbent. The number of such aminoalkyl groups on the agarose gel will affect the amount of hepatitis B surface antigen adsorbed during the hydrophobic chromatography.

Thereafter, the mixture containing the hepatitis B surface antigen is poured over a column containing the so-treated agarose gel. Generally, the rate at which the mixture is poured will depend upon the nature of the agarose gel and the amount of aminoalkyl groups thereon. However, the flow rate is generally the normal flow rate of the liquid and no pressure is imposed upon the liquid to force it to flow through the chromatography column at a faster rate. Generally, the flow rate of the mixture containing the hepatitis B surface antigen is between 0.75 and 1 times the normal flow rate of a liquid through the agarose gel containing column.

The amount of mixture which is passed therethrough depends upon the extent to which the hepatitis B surface angiten has been subjected to a previous purification. Thus, it has been found that when hepatitis B surface antigen has been partially prepurified by chromatography on insolubilized concanavalin A on Sepharose, the amount of such material which can be applied to the aminoalkyl-agarose gel of the invention can be up to about 70% of the volume of the column. If, however, the material containing the hepatitis B surface antigen has not undergone a previous partial purification, the amount which can be passed over the agarose gel is substantially decreased. Generally speaking, the amount of hepatitis B surface antigen containing mixture which is passed over the treated agarose in the chromatography column is equivalent to 10 to 100% of the volume of the column.

The hepatitis B surface antigen is usually present in a proteinaceous mixture, especially a mixture such as serum or plasma. It should be understood, however, that hepatitis B surface antigen can be removed from other mixtures such as aqueous mixtures and particularly from waste water and the like.

The treatment described effects a nearly selective removal of the hepatitis B antigen onto the agarose gel allowing other material to pass through the column and to be discarded or further treated. Thereafter, the hepatitis B surface antigen is removed from the agarose gel by the use of an eluting agent. Generally speaking, the eluting agent can be an aqueous solution of chaotropic ions. Generally, they are present at a concentration lower than that at which the antigen will become denatured. A 3–4 molar solution of chaotropic ions is suitable for this purpose.

Suitable chaotropic ions include iodides, thiocyanates, perchlorates, nitrates and others disclosed by Hatefi and Hanstein, 1969; Solubilization of Particulate Proteins and Non-electrolytes by Chaotropic Agents, *Proceedings of the National Academy of the United States of America*, 62 1129–1136, the disclosure of which is hereby incorporated herein by reference.

By such an elution process, there is recovered a mixture of hepatitis B surface antigen, residual serum proteins and eluant. Generally, this mixture is subjected to a subsequent process designed to ultimately recover the surface antigen in a form where it can be used in an active vaccine. However, if desired, the hepatitis B surface antigen can be recovered as a partially purified product by subjecting the eluate to an ultrafiltration process.

In order to more fully illustrate the nature of the invention and the manner of practicing the same, the following examples are presented:

EXAMPLE 1

Omega-aminoalkyl-Sepharose 4B was prepared by mixing 40 ml. of a 0.25 molar solution of alpha, omega-diaminoalkane having the general formla $NH_2-(CH_2)_n-NH_2$, wherein $n$ was a whole number from 1 to 10. The diaminoalkane had been dissolved in a mixture of N,N-dimethylformamide and water 1:1 which contained 0.1 molar $NaHCO_3$ and was adjusted to a pH between 11.0 and 9.0 by addition of HCl, with 3 grams of CNBr-activated Sepharose 4B obtained commercially from Pharmacia, Uppsala, Sweden. The CNBr-activated Sepharose 4B remained in contact with the alpha, omega-diaminoalkane at 23°C overnight. The diaminoalkane had been obtained from Aldrich Chemical Company, Milwaukee, Wisconsin, and from K & K Laboratories, Plainview, New York.

The aminoalkylated derivatives were washed on a filter with 50 ml. of distilled water followed by three alternate washings, each with 0.1 molar borate, 1 molar NaCl (pH 8.0) and 0.1 molar acetate, 1 molar NaCl (pH 4.0). A portion of the 1,10-diaminodecane precipitated during the reaction with the CNBr-activated Sepharose. In that case, the N,N-dimethylformamide in admixture with 0.1 molar $NaHCO_3$ was employed as the first wash to dissolve the precipitated diamine. Several experiments were conducted to determine the ability of the so-treated agarose gel to further purify hepatitis B surface antigen which had been subjected to a prior purification process. Protein in fractions after chromatography was determined spectrophotometrically at 280 nm. Thiocyanate was determined in the form of its complex with $Fe^{+++}$. One ml of 400-fold diluted samples was mixed with 1 ml of a solution containing 1 ml of $Fe(NO_3)_3$ in 1 ml of 0.5 N HCl. The optical density was measured at 480 nm. The number of aminoalkyl groups linked to agarose was determined spectrophotometrically with picrysulphonic acid in accordance with Failla and Santi, 1973. A simple method for quantitating ligands covalently bound to agarose beads. *Analytical Biochemistry*, 52, 363–368.

In preliminary experiments hepatitis B surface antigen partially purified by chromatography on concanavalin A-Sepharose (Neurath, Prince and Lippin, 1973, supra) and suspended in 0.01 molar tris pH 7.2 (TB) was applied to columns of various gamma-aminoalkylagaroses. These agarose derivatives differed in the number of carbon atoms in the hydrocarbon side chain but contained approximately the same number of ligands bound per ml of agarose gel, generally 7.5 to 10.3 $\mu$ mols.

It was then determined to what extent proteins and hepatitis B antigen eluted from the column. If both of these materials pass through the column, then the omega-aminoalkyl groups on the agaroses are not useful in the selective adsorption of the hepatitis B surface antigen. The amounts of serum protein and hepatitis B surface antigen which eluted from the column were measured and plotted on a graph which is the subject of FIG. 1. FIG. 1 shows that the elution of both serum proteins and hepatitis B surface antigen was shifted to higher concentrations of sodium chloride with increasing number of carbon atoms in the amonoalkyl groups. While the recovery of protein is about 100% for $C_5$-$C_8$ omega-aminoalkyl-containing agaroses and 90% for $C_9$ or $C_{10}$ omega-aminoalkyl-containing agaroses, the elution of hepatitis B surface antigen decreased drastically with increasing carbon number and dropped to only 9 and 3% for $C_9$ and $C_{10}$ omega-aminoalkyl-containing agaroses, respectively.

Attempts wre made to elute hepatitis B surface antigen with buffers of various pH (2.2 and 10.85) or with solutions containing organic solvents (1 to 25% (v/v) ethanol, 10 to 40% (v/v) dimethylformamide); detergents (0.1% sodium deoxycholate, 0.1% Tween 80) or urea (1 to 7 M) were all unsuccessful.

Thereafter, aqueous solutions of chaotropic salts were employed owing to their known ability to impart lipophilic properties to water. Complete elution of hepatitis B surface antigen was obtained with the use of a 4 molar aqueous sodium iodide solution or with the use of a 4 molar sodium thiocyanate solution. In subsequent experiments, 4 molar sodium thiocyanate was used for elution of hepatitis B surface antigen to avoid any potential difficulties due to the presence of free iodine in solutions of sodium iodide.

It was found that the $C_9$ and $C_{10}$ aminoalkyl-containing agarose gels are remarkable in the partially selective removal of hepatitis B surface antigen from a proteinaceous mixture containing the same. It was also observed that this property is specific to $C_9$ and $C_{10}$ omega-aminoalkyl groups and is not a property of all omega-aminoalkyl-containing agarose gels of whatever carbon chain length.

EXAMPLE 2

Hepatitis B surface antigen was applied to a 0.9 × 10.5 centimeter column of omega-aminodecyl-Sepharose 4B. The column was washed with 30 ml. of 0.8 M NaCl followed with 4 M NaSCN. Fractions of 2.5 ml each were collected and analyzed for protein content, hepatitis B surface antigen content and NaSCN. Preparations of the antigen were chromatographed to determine the capacity of the column corresponding to the maximum volume for each preparation which can be applied to the column in terms of the percentage of the column volume. The degree of purification was also determined.

Several different samples containing hepatitis B surface antigen were passed over the omega-aminodecyl containing Sepharose 4B. One sample was obtained by passing serum over an insolubilized concanavalin A-Sepharose and eluting the same therefrom. It ws found that the capacity of the column for this sample, i.e., the partially purified hepatitis B surface antigen was 70%. It was also found that the hepatitis B antigen was purified 13-fold, based upon its purity in the already partially purified form and 130-fold compared with the original serum.

Another sample was obtained by precipitation with polyethyleneglycol by which Dane particles and filaments could be removed. This partially purified sample was purified still further so that the purification ranged between 18- and 66-fold, the purification being by passing the prepurified material over the omega-aminodecyl Sepharose 4B. It was determined that the capacity of the column for such a partly prepurified material was 25% of the column volume. Several different experiments were conducted with the prepurified hepatitis B antigen and the results of one experiment are shown in FIG. 2.

A third testing sample consisted of hepatitis B surface antigen-positive serum. This material was purified 20-fold and it was determined that the capacity of the column for this material was about 10% of the column volume. The results of all of the purifications of this Example were obtained employing an omega-aminodecyl Sepharose 4B containing 10.9 micromoles of aminoalkyl groups per ml of treated agarose gel. Similar results were obtained with gamma-aminononyl Sepharose which contained 6.1 micromoles of gamma-aminononyl groups per ml of agarose and had proportionately a lower capacity to bind the hepatitis B surface antigen.

EXAMPLE 3

Attempts were made to replace the commercial CNBr-activated Sepharose 4B with Sepharose 4B activated in the laboratory with CNBr at a pH of 11.0. The resulting omega-aminoalkyl agarose compounds adsorbed the surface antigen and a portion of the serum proteins irreversibly. The insolubility of these derivatives in 50% (v/v) acetic acid at 75°C (conditions appropriate for melting of agarose for determination of the bound ligands) suggest a higher degree of cross-linking compared with that of substituted agaroses prepared from commercial CNBr-activated Sepharose which dissolve under these conditions.

In another experiment gamma-aminodecyl agarose obtained from Miles-Yeda, Rehovot, Israel, was tested to determine its ability to adsorb hepatitis B surface antigen preferentially when the same is in a proteinaceous serum. About 35% of the hepatitis B surface was recovered by hydrophobic chromatography performed in the manner described above. The omega-aminodecyl agarose was partly soluble in 50% acetic acid at 75°C.

EXAMPLE 4

An activated agarose having the desired characteristics was prepared by mixing appropriate volumes of a 50% (v/v) slurry of Sepharose 2B in 0.1 M $Na_2HPO_4$ and a freshly prepared solution of CNBr in acetonitrile (300 mg/ml). pH was maintained at 9.8 to 10.5 for 10 minutes by addition of two normal sodium hydroxide. The gel was washed with 0.1 molar sodium bicarbonate.

The so-prepared CNBr-activated Sepharose 2B was treated with alpha, omega-diaminononane to insert omega-aminononyl groups on the activated Sepharose. The ability of the so-treated aminoalkyl agarose was tested to determine to what extent it would selectively adsorb hepatitis B surface antigen particles. A mixture of the antigen and protein was passed over the so-treated aminoalkyl agarose while in a column. Thereafter, the hepatitis B surface antigen was eluted with 4 M NaSCN. The partially purified antigen was concentrated by ultrafiltration without prior removal of NaSCN and the purification was completed by density gradient centrifugation.

EXAMPLE 5

Chromatography on aminoalkyl agaroses containing 4 to 6 carbon atoms was tested. Whereas these materials had previously been reported to be useful in the purification of some enzymes, it was discovered that they were virtually useless in the selective removal of hepatitis B surface antigen from serum proteins.

Figure 1:
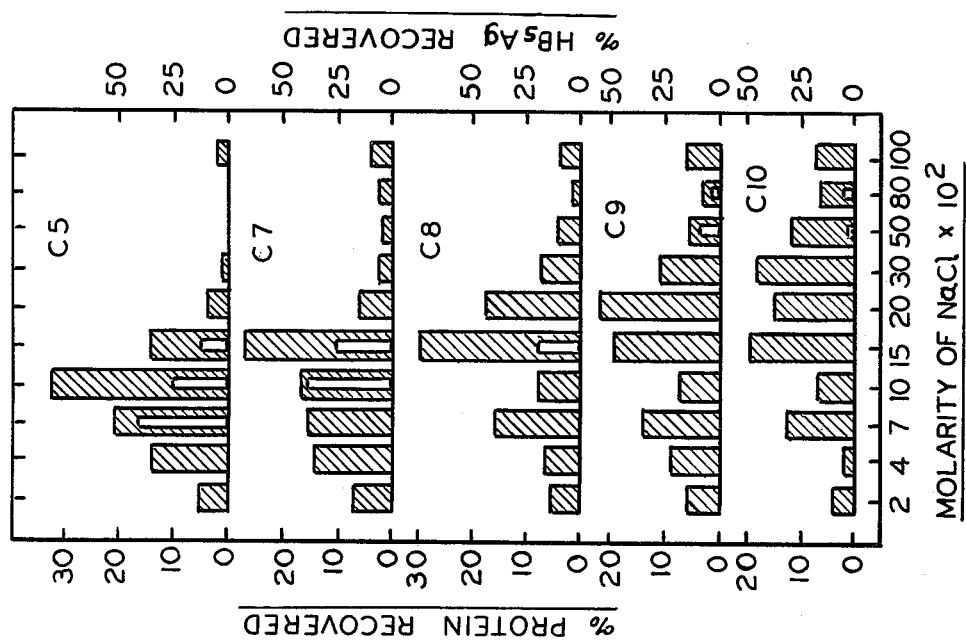

In FIG. 1 the amounts of protein recovered and hepatitis B surface antigen recovered are reported. FIG. 1 reports the results of experiments carried out with $C_5$ and $C_{7-10}$ omega-aminoalkyl agarose columns. The hepatitis B surface antigen was contained in a partially purified mixture and 1 ml of the same was passed over the aminoalkyl-agarose. The recovery of proteins and hepatitis B antigen following elution of the gamma-aminoalkyl agarose columns (0.9 × 3.5 cm) was determined, the elution being performed with solutions (6 ml each) containing increasing quantities of NaCl in 0.01 M tris buffer pH 7.2. The 1 molar NaCl solution was in 0.1 molar phosphate having a pH of 10.85. The data in FIG. 1 show that while proteins are eluted from a $C_5$ omega-aminoalkyl agarose gel, substantial quantities of the hepatitis B surface antigen are also eluted, particularly at lower molarity values from the NaCl solution. This means that the $C_5$ omega-aminoalkyl Sepharose does not selectively adsorb the hepatitis B antigen at least to a sufficient extent to be practical for the purification of the antigen when contained in a proteinaceous mixture.

Similarly, when a $C_7$ omega-aminoalkyl Sepharose is tested, substantial quantities of both protein and antigen are recovered, indicating that the material is not selective for the antigen. The $C_8$ sample is substantially better but if 0.15 M NaCl was used for elution a substantial quantity of the antigen was also recovered together with the protein. This is undesirable.

However, when $C_9$ and $C_{10}$ omega-aminoalkyl agarose gels are tested, essentially no antigen is recovered. This means that the material preferentially adsorbs the antigen while allowing the elution of protein by solutions of NaCl. The antigen can be recovered by the use of a separate eluant, e.g., a solution of chaotropic ions.

In FIG. 2, the separation of hepatitis B antigen from the major portion of serum proteins by chromatography on omega-decyl Sepharose is reported.

In these experiments, after the hepatitis B sample was passed through the omega-aminodecyl Sepharose B column measuring 0.9 × 10.5 cm., the column was washed with 30 ml of 0.8 molar sodium chloride followed with 4 molar sodium thiocyanate. Fractions of 2.5 ml each were collected and analyzed for protein and hepatitis B antigen content.

The hepatitis B surface antigen was completely recovered in the eluant. This indicates that the chaotropic ion solution (=SCN) is an effective eluant for the removal of hepatitis B surface antigen from omega-aminoalkyl agarose.

FIG. 2 also shows a dramatic increase in the optical density of the eluant in samples 3 to 8 corresponding to proteins other than hepatitis B surface antigen. This indicates a substantial purification of hepatitis B antigen.

What is claimed is:

1. A process for separating hepatitis B surface antigen from a mixture containing the same, which comprises passing said mixture over an agarose gel containing $C_9$ or $C_{10}$ terminal aminoalkyl groups to thereby deposit on said gel said hepatitis B surface antigen while allowing other components of said mixture to pass therethrough and thereafter eluting said hepatitis B surface antigen by passing eluting agent comprising an aqueous solution of chaotropic ions present in said solution at a concentration lower than that at which the antigen will become denatured over said agarose gel.

2. A process according to claim 1 wherein said hepatitis B surface antigen is in a mixture of serum protein.

3. A process according to claim 1 wherein the chaotropic ion is selected from the group consisting of sodium iodide, sodium thiocyanate, sodium perchlorate and sodium nitrate.

4. A process according to claim 1 wherein the hepatitis B surface antigen is in a mixture which has been subjected to prepurification by passing a mixture of the antigen and other proteins over an insolubilized concanavalin A agarose gel and eluted.

5. A process according to claim 1 wherein the hepatitis B surface antigen containing mixture is one obtained following precipitation of an antigen containing mixture employing polyethylene glycol to remove Dane particles and filaments.

6. A process according to claim 1 wherein the mixture containing the hepatitis B surface antigen is a hepatitis B surface antigen-positive serum.

7. A process according to claim 3 wherein the chaotropic ion containing solution is a 3–4 M aqueous solution of NaSCN.

* * * * *